US00PP17483P3

(12) United States Plant Patent
Pecota et al.

(10) Patent No.: US PP17,483 P3
(45) Date of Patent: Mar. 13, 2007

(54) ORNAMENTAL SWEETPOTATO PLANT NAMED 'SWEET CAROLINE RED'

(50) Latin Name: *Ipomoea batatas*
Varietal Denomination: Sweet Caroline Red

(75) Inventors: Kenneth Pecota, Raleigh, NC (US); G. Craig Yencho, Raleigh, NC (US); Charles Newell Hancock, Jr., Bear Creek, NC (US)

(73) Assignee: North Carolina State University, Raleigh, NC (US)

( * ) Notice: Subject to any disclaimer, the term of this patent is extended or adjusted under 35 U.S.C. 154(b) by 91 days.

(21) Appl. No.: 10/951,564

(22) Filed: Sep. 28, 2004

(65) Prior Publication Data

US 2006/0010541 P1 Jan. 12, 2006

(30) Foreign Application Priority Data

Jul. 8, 2004 (CA) ..... PBR 04-4296

(51) Int. Cl.
*A01H 5/00* (2006.01)

(52) U.S. Cl. ..... Plt./258

(58) Field of Classification Search ..... Plt./258
See application file for complete search history.

*Primary Examiner*—Kent Bell
(74) *Attorney, Agent, or Firm*—Myers Bigel Sibley & Sajovec, PA

(57) ABSTRACT

*Ipomoea batatas* 'Sweet Caroline Red' has very distinct coloration; new shoots are yellow-green in color and transition to a dark burgundy-red color when mature. The stems and petioles of the mature plant are also dark burgundy-red in color. The leaves are large, palmately lobed and veined. 'Sweet Caroline Red' has a moderately compact growth habit and is a low, mounding-to-trailing plant with an overall oval shape that is suitable for use as a ground cover or in containerized landscape settings. The plant also has excellent vigor.

2 Drawing Sheets

Latin name of the genus and species: The latin name of the novel, ornamental plant variety disclosed herein is *Ipomoea batanas* (L.) Lam.

Variety denomination: The inventive cultivar of *Ipomoea batatas* disclosed herein has been given the variety denomination 'Sweet Caroline Red'.

RELATED APPLICATION INFORMATION

This application claims the benefit of Canadian Plant Breeders' Rights Application Serial No. 04-4296, filed in the Canadian Plant Breeders' Rights Office on Jul. 8, 2004; the disclosure of which is incorporated herein by reference in its entirety.

BACKGROUND OF THE INVENTION

*Ipomoea* species are members of the morning glory family Convolvulaceae. *Ipomoea batatas*, the cultivated species, is commonly referred to as the white or yellow sweetpotato and the orange yam. The plants are typically fast growing vines possessing a wide variety of leaf shapes ranging from palmate and deeply lobed to cordate or triangular shaped leaves with no lobes. These ornamental species produce storage roots like the common sweetpotato, but they are generally not as attractive and they are not palatable. Late in the growing season, tubular flowers appear which are similar to morning glories, but plantings are dominated by the appearance of the foliage. The plants are highly desirable due to their ability to grow under varied stress conditions, cover a large space, and last the entire growing season. Moreover, these plants have few insect or disease problems.

There are currrently six popular types of *Ipomoea batatas* ornamental sweetpotatoes that are being cultivated primarily for their annual, summer vines in landscaping applications. These six cultivars are: 'Blackie' (not patented), having dark purple-black foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spades'), having heart-shaped leaves with burgundy purple color; 'Tricolor' (not patented; also known as 'Pink Frost'), is a variegated plant which has pale green, white, and pink-margined leaves; and 'Lady Fingers' (unpatented), which has medium green, dainty leaves divided into long, thin, fingerlike lobes which are complemented by burgundy stems and veins.

*Ipomoea batatas* 'Margarita' has recently been released in the United States, and has become widely used as a landscape annual. It is not suitable for mixed containers as this variety exhibits a very vigorous growth and tends to outcompete other species. Another popular variety is 'Blackie', a vigorous purple-leaved clone which is also unsuited to containerized gardens. See Armitage. A. M. and J. M. Garner, (2001) *Ipomoea batatas* 'Margarita'. *HortScience* 36:178.

Therefore, to meet the current horticultural demand, it is desirable to produce new, more robust cultivars of ornamental sweetpotato with attractive foliage colors. leaf shapes, and plant architectures. In addition, it would be advantageous to develop cultivars of ornamental sweetpotato exhibiting a more compact growth, and which do not out-compete othere species in mixed containers.

*Ipomoea batatas* 'Sweet Caroline Light Green' (U.S. Plant Pat. No. 15,028), 'Sweet Caroline Green' (U.S. Plant Pat. No. 15,056), 'Sweet Caroline Bronze' (U.S. Plant Pat.

No. 15,437 and 'Sweet Caroline Purple' (U.S. Plant Pat. No. 14,912) are recently introduced cultivars developed in North Carolina that are characterized by compact growth habit, moderate to deeply lobed palmate leaves, and attractive foliage color.

The present invention relates to a new and distinct variety of *Ipomoea batatas* named 'Sweet Caroline Red' that has a dark burgundy-red coloration on mature foliage, which is not currently available in ornamental sweetpotatoes. The variety is suitable for use as a lanscape or containerized plant.

Lineage. The *Ipomoea batatas* 'Sweet Caroline Red' cultivar originated from a conventional cross between *Ipomoea batatas* cultivars 'Sweet Caroline Bronze' (the female parent) and NC138-1ORN (the male parent; not patented) conducted in the Winter of 2001–2002 at the Horticultural Greenhouses located at North Carolina State University, Raleigh, N.C., USA. 'Sweet Caroline Bronze' originated from a conventional cross between the cultivars 'Sulfur' (the female parent; not patented) and NCSXBR5-18ORN (the male parent; not patented). NCSXBR5-18ORN originated from a 'Sulfur' (the female parent) by 'Blackie' (the male parent) cross. NC138-1ORN, the male parent of 'Sweet Caroline Red', resulted from a 'Sulfur' (the female parent) by 'Blackie' (the male parent) cross. Seeds from this cross were planted in the Horticultural Greenhouses in Spring 2002. The individual plant now known as *Ipomoea batatas* 'Sweet Caroline Red' was selected in June 2002 because of its combination of exceptional features, and has been propagated asexually since that time.

Asexual Reproduction. Since its selection, *Ipomoea batatas* 'Sweet Caroline Red' has been asexually reproduced at the Horticultural Greenhouses located in Raleigh, N.C. (USA) predominantly by vegetative propagation of vine cuttings. The combination of characteristics disclosed herein for *Ipomoea batatas* 'Sweet Caroline Red' has remained stable and the plant reproduces true to type through successive generations of asexual reproduction.

SUMMARY OF THE INVENTION

*Ipomoea batatas* 'Sweet Caroline Red' has a very distinct coloration; new shoots are yellow-green in color and transition to a dark burgundy-red color when mature. The stems and petioles of the mature plant are also dark burgundy-red in color. To the best of the inventors' knowledge, this color is not found elsewhere in ornamental sweetpotatoes. The leaves are large, palmately lobed and veined. 'Sweet Caroline Red' has a moderately compact growth habit and is a low, mounding-to-trailing plant with an overall oval shape that is suitable for use as a ground cover or in containerized landscape settings. The plant also has excellent vigor.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas.*

DETAILED BOTANICAL DESCRIPTION

The following is a detailed description of the botanical characteristics of the new and distinct cultivar of *Ipomoea batatas* plant known by the cultivar name *Ipomoea batatas* 'Sweet Caroline Red'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 15-week-old specimens grown individually in six-inch pots. The plants were grown in Lompoc, Calif., under commercial practice in a polycarbonate-covered greenhouse during the winter and spring with day and night temperatures ranging between 21.1–23.8° C. and 15.6–18.3° C., respectively, and light levels of about 4,000–8,000 foot-candles. *Ipomoea batatas* 'Sweet Caroline Red' has not been observed under all possible environmental conditions; therefore, the phenotype may vary somewhat with variations in the environment such as season, temperature, light intensity, day length, cultural conditions, and the like, without however any variance in the genotype.

Technical Description of the Variety

Figure 1:
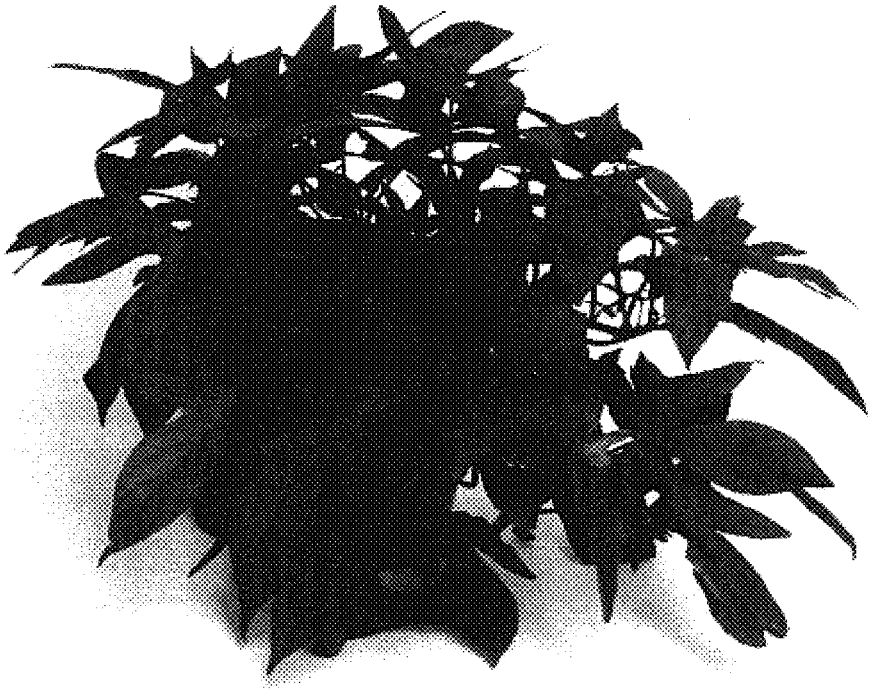
FIG. 1 is a color photograph of a typical plant of the *Ipomoea batatas* 'Sweet Caroline Red' grown in a six-inch container under commercial greenhouse conditions for 15 weeks.

Above-Ground Structure and Coloration. Overall, 'Sweet Caroline Red' is a low, mounded-to-trailing, outwardly-spreading, herbaceous plant with an oval shape (FIG. 1). The stems are horizontal and trailing with leaves tending to face up. The plant has an average height of about 20 cm and an average area of spread of about 40×46 cm after 15 weeks of growth in the greenhouse conditions described above.

Branching Habitat. Good branching with approximately 4 lateral branches coming off the stem. Pinching is not required to stimulate branching. Many latent axillary stems can form with pinching of shoot tips. Axillary stems are identifiable as they contrast with the red color of mature stems. Color: Dark burgundy-red (187A).

Vegetative Lateral Branches. Length: ~24.0 cm. Diameter: ~0.5 cm. Internodes have an average length of ~1.5 cm. Color: Dark burgundy-red (187A).

Stem. Round and smooth with very good strength. Stem aspect is mostly horizontal. Some scattered white pubescence is evident near shoot tips. Stem diameter is ~0.5 cm, with stem length averaging ~ 24 cm after 15 weeks of growth in the greenhouse conditions described above. Stem Color: Dark burgundy-red (187A).

Petiole. Often twisted at base to orient leaf blade to face up on horizontal stem. Length: ~10.0 cm. Diameter: ~0.3 cm. Color: Dark burgundy-red (187A).

Figure 2:
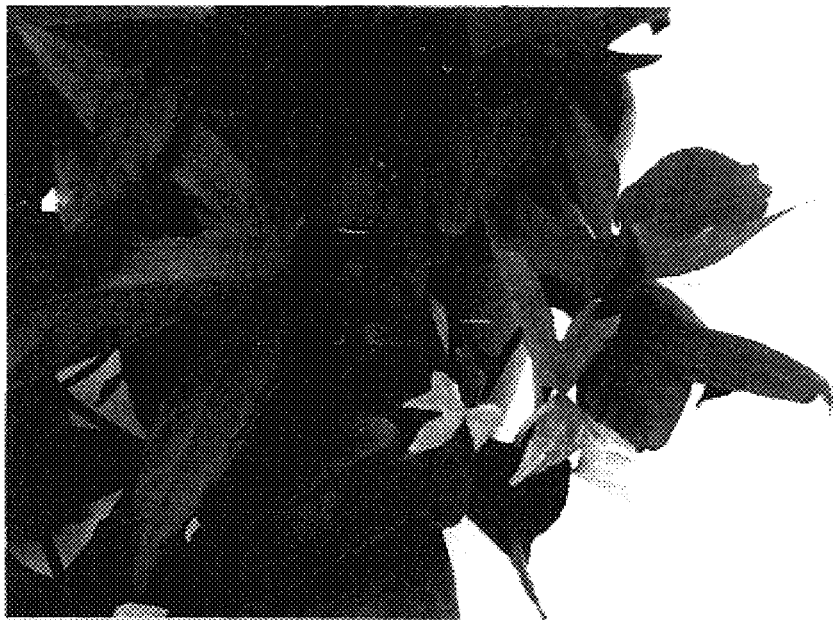
FIG. 2 is a color photograph showing both new and mature foliage produced by *Ipomoea batatas* 'Sweet Caroline Red' grown in a six-inch container under commercial greenhouse conditions for 15 weeks.

Foliage. Leaves are alternate, simple and palmately lobed and veined (FIG. 2). Quantity: Densely foliated, with ~18 leaves per lateral branch. Mature leaf length: ~12.5 cm. Mature leaf width: ~12.5 cm. Leaf margin is entire with deep sinuses. One long terminal lobe and 1–2 shorter lateral lobes on each side of the mid-vein. Terminal lobe width: ~4.0 cm. Lateral lobe width: ~1.8–2.3 cm. Leaf apex: broadly acute. Leaf base: Acute. Leaf has a smooth texture and matte finish. Venation is palmate. Color: see Table 1.

TABLE 1

| Leaf Structure | Upper Surface | Lower Surface |
|---|---|---|
| Young Leaf | Yellow-Green; 144A | Yellow-Green; 144A |
| Intermediate Leaf | Bronze; similar to 199A tinged with 144A* | Bronze; similar to 199A tinged with 144A* |
| Mature Leaf | Very Dark Burgundy Red; 187A | More Green than 187A* |
| Vein | 187A | 187B |

*The color does not match any color provided in The Royal Horticultural Society Colour Chart.

Color Variation. *Ipomoea batatas* 'Sweet Caroline Red' has a very striking color combination (Table 1). The new shoots are yellow-green, and as the leaves mature, they transition to a bronze and then develop the characteristic very dark burgundy-red color at maturity.

Leaf color of *Ipomoea batatas* 'Sweet Caroline Red' can range from red to reddish-burgundy depending on the environment. Lower temperatures favor anthocyanin pigment development and plants tend to be more burgundy. Higher temperatures result in a plant that is more reddish than burgundy.

Flowers. *Ipomoea batatas* 'Sweet Caroline Red' flowers sporadically throughout the season in response to a variety of stressful conditions (e.g., drought, nutrient stress, cloudy weather). Flowering is enhanced by shorter day lengths, but the precise photoperiod for flower induction is currently unknown. The inflorescence is generally a cyme in which there is one solitary peduncle. Peduncles (Color: 187A) are purple, averaging 46 mm long from mature leaf axils with an average diameter of 2 mm. Usually buds of the first and second order are developed, but often, single flowers are produced. Buds (Color 181D) are rose/pink colored, ovate, and around 17 mm in length and 5 mm in diameter, 24 hours before opening. The corolla is composed of five fused petals that form a funnel with a rounded limb. Corolla width: ~4.2 cm, corolla length: ~4.0 cm. The corolla's fragrance is slight to none. The corolla and buds sometimes have a slightly crinkled appearance. The limb color is light lavender, while the outer throat color is lavender and the inner throat color is purple. Inner limb color: 84B, Outer limb color: 84C, Inner throat color: 77A, Outer throat color: 76B. There are five sepals, with an average length of 9.7 mm and width of 3.9 mm. The sepals are obovate with an oblong apex and dark purple in color. Outer sepal color: 59A, Inner sepal color: 59A. Each flower has one pistil with a light pink colored style (Color: 73D). The stigma is cream colored (Color 155A) and averages about 2 mm wide and 20 mm long. The stigma is exerted relative to the stamens. The ovary is yellow (Color: 151D) and superior with two locules that contain one or two ovules. At the base of the ovary there are orange basal glands (Color: 163A) containing nectar continuing completely up the ovary. There are five cream colored anthers (Color: 158D) that are approximately 2 mm long. Pollen (Color: 158D) is scarce. True seed are difficult to obtain, even with compatible crosses. There is some variation in flower size and color, depending on the environmental conditions.

Figure 3:
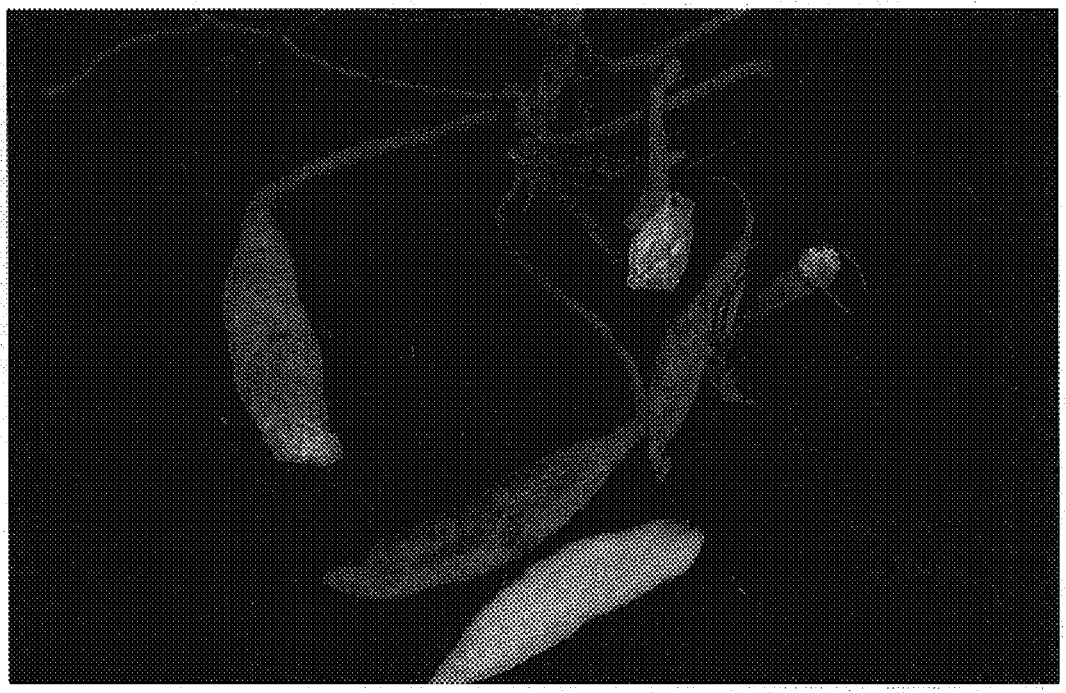
FIG. 3 is a color photograph showing typical storage roots produced by Sweet Caroline Red 123 days after planting. Plants were planted as five-hill plots spaced 30.5 cm apart in the row in Clinton, N.C. USA.

Below-Ground Structure. Plants form small underground storage roots that are highly malformed and do not meet USDA Sweetpotato Storage Root Grade Standards (FIG. 3). Skin color is cream (159A) with a pink blush (70B) and flesh color is cream (159C) with light orange mottling (24B). Environmental conditions (temperature, water, light, etc.) have the potential to affect storage root development and shapes, as well as flesh and skin color.

Growth Conditions. *Ipomoea batatas* 'Sweet Caroline Red' has excellent vigor, a moderate-to-fast growth rate, and is very adaptable to container culture. In locales with mild winter conditions, *Ipomoea batatas* 'Sweet Caroline Red' will grow perennially; otherwise it is an annual plant. Similar to cultivated sweetpotatoes, the foliage of 'Sweet Caroline Red' has good durability under stress conditions.

Disease or Pest Resistance. 'Sweet Caroline Red' is susceptible to Sweetpotato Feathery Mottle Virus and most insects that commonly feed on the foliage of sweetpotatoes such as Japanese beetles and tortoise beetles.

Comparison with Other *Ipomoea batatas* Cultivars

Compared with the other cultivars of ornamental sweetpotato, *Ipomoea batatas* 'Sweet Caroline Red' is distinct. The coloration of the foliage is unique, and there are no suitable comparators among existing cultivars of *Ipomoea batatas* known to the inventors.

Likewise, in a comparison with the parental strains, 'Sweet Caroline Red' is quite distinct from each parent (Table 2).

TABLE 2

| Characteristic | 'Sweet Caroline Red' | Female Parent NC138-1ORN | Male Parent 'Sweet Caroline Bronze' |
|---|---|---|---|
| Foliage Color | Red to Burgundy-Red | Light Bronze to Bronze | Bronze to Red |
| Leaf Shape and Size | Moderately to Deeply Lobed, Medium Sized | Moderately Lobed, Very Large | Moderately to Deeply Lobed, Medium Sized |
| Plant Habit | Moderately Branched | Relatively Few Branches | Moderately to Well Branched |

Herbarium Voucher

A voucher of 'Sweet Caroline Red' will be deposited into the Herbarium of North Carolina State University in Raleigh, N.C., USA upon patenting.

What is claimed is:

1. A new and distinct cultivar of *Ipomoea batatas* plant named 'Sweet Caroline Red', substantially as illustrated and described herein.

* * * * *

UNITED STATES PATENT AND TRADEMARK OFFICE

CERTIFICATE OF CORRECTION

PATENT NO. : PP 17,483 P3
APPLICATION NO. : 10/951564
DATED : March 13, 2007
INVENTOR(S) : Pecota et al.

It is certified that error appears in the above-identified patent and that said Letters Patent is hereby corrected as shown below:

On Title Page,
Column 2 , Line 26: Please correct "colors. Leaf" to read --colors, leaf--

Column 3, Line 27: " 'Blackie' (the male parent) cross." should be changed to --'S x BL-R6-1'.--

Column 5, Line 52-54: Please correct "The stigma is cream colored (Color 155 A) and averages about 2mm wide and 20 mm long." To read -- The stigma is cream colored (Color 155 A).--

Table 2,
Column 3: Please correct the title to read --Male Parent NC138-1ORN--
Column 4: Please correct the title to read --Female Parent 'Sweet Carline Bronze'--

Signed and Sealed this

Twelfth Day of June, 2007

JON W. DUDAS
*Director of the United States Patent and Trademark Office*

UNITED STATES PATENT AND TRADEMARK OFFICE

CERTIFICATE OF CORRECTION

PATENT NO. : PP 17,483 P3
APPLICATION NO. : 10/951564
DATED : March 13, 2007
INVENTOR(S) : Pecota et al.

It is certified that error appears in the above-identified patent and that said Letters Patent is hereby corrected as shown below:

On Title Page,
Column 2, Line 26: Please correct "colors. Leaf" to read --colors, leaf--

Column 3, Line 27: " 'Blackie' (the male parent) cross." should be changed to --'S × BL-R6-1'.--

Column 5, Line 52-54: Please correct "The stigma is cream colored (Color 155 A) and averages about 2mm wide and 20 mm long." To read -- The stigma is cream colored (Color 155 A).--

Table 2,
Column 3: Please correct the title to read --Male Parent NC138-1ORN--
Column 4: Please correct the title to read --Female Parent 'Sweet Caroline Bronze'--

This certificate supersedes Certificate of Correction issued June 12, 2007.

Signed and Sealed this

Fourteenth Day of August, 2007

JON W. DUDAS
*Director of the United States Patent and Trademark Office*